United States Patent [19]

Homan et al.

[11] 4,272,415

[45] Jun. 9, 1981

[54] COMPOSITIONS INCLUDING MERCAPTOORGANOPOLYSILOXANES AND METAL SALTS OF CARBOXYLIC ACIDS

[75] Inventors: Gary R. Homan; Chi-Long Lee, both of Midland, Mich.

[73] Assignee: Dow Corning Corporation, Midland, Mich.

[21] Appl. No.: 99,302

[22] Filed: Dec. 3, 1979

[51] Int. Cl.$^3$ ............................................. C08L 91/00
[52] U.S. Cl. ................................. 260/18 S; 204/159.13; 528/14; 528/15; 528/30; 528/43; 260/37 SB
[58] Field of Search .................. 260/18 S, 37 SB; 528/30, 15, 14, 43; 204/159.13

[56] References Cited

U.S. PATENT DOCUMENTS

| | | |
|---|---|---|
| 3,445,419 | 5/1969 | Vanderlinde ......................... 260/37 |
| 3,655,713 | 4/1972 | Le Grow ........................... 260/448.2 |
| 3,816,282 | 6/1974 | Viventi ............................. 204/159.13 |
| 3,873,499 | 3/1975 | Michael et al. ............... 260/45.95 E |
| 4,039,504 | 8/1977 | Homan et al. ..................... 260/37 SB |
| 4,039,505 | 8/1977 | Homan et al. ..................... 260/37 SB |
| 4,064,027 | 12/1977 | Gant ................................. 204/159.13 |
| 4,066,603 | 1/1978 | Homan et al. ..................... 260/37 SB |
| 4,070,328 | 1/1978 | Homan et al. ..................... 260/37 SB |
| 4,070,329 | 1/1978 | Homan et al. ..................... 260/37 SB |

FOREIGN PATENT DOCUMENTS 2008426 2/1970 Fed. Rep. of Germany.

*Primary Examiner*—Melvyn I. Marquis
*Attorney, Agent, or Firm*—Roger H. Borrousch

[57] ABSTRACT

Oxygen curable compositions are provided by mixing mercaptoorganopolysiloxanes with a metal salt of a carboxylic acid wherein the metal is iron, copper, cobalt, manganese, or nickel.

5 Claims, No Drawings

COMPOSITIONS INCLUDING MERCAPTOORGANOPOLYSILOXANES AND METAL SALTS OF CARBOXYLIC ACIDS

BACKGROUND OF THE INVENTION

1. Field of the Invention

This invention relates to oxygen curable compositions including mercaptoorganopolysiloxanes and carboxylic acid salts of metals.

2. Description of the Prior Art

Applicants' U.S. Pat. Nos. 4,039,504 and 4,039,505 are generally directed to compositions curable to elastomers at room temperature or with heat. These compositions are prepared from mixtures of certain polymethylvinylsiloxanes and mercaptoorganopolysiloxanes with an organic peroxide, and optionally a filler.

Applicants' U.S. Pat. No. 4,070,329 discloses compositions prepared from mixtures of mercaptoorganopolysiloxanes, and organic peroxide catalysts. Applicants' U.S. Pat. No. 4,070,328 discloses compositions prepared from mixtures of mercaptoorganopolysiloxanes, organic hydroperoxide, and selected nitrogen compounds. The compositions prepared according to these references can be used as sealants which rapidly cure to elastomers with non-tacky surfaces.

Numerous other prior art references are directed to compositions involving mercaptoorganopolysiloxanes and mixtures thereof with alkenyl-containing siloxanes as well as to curing systems employing electromagnetic and particulate radiation. These references include: U.S. Pat. No. 3,445,419; U.S. Pat. No. 3,816,282; U.S. Pat. No. 3,873,499; German Pat. publication (OLS) 2,008,426; U.S. Pat. No. 4,064,027; U.S. Pat. No. 4,066,603; and U.S. Pat. application Ser. No. 663,326, filed Mar. 3, 1976, by Gary N. Bokerman and Robert E. Kalinowski, entitled "Method of Curing Thick Section Elastomers" and assigned to the same assignee as the present invention now abandoned. The disclosures of the above-identified patents and applications are specifically incorporated by reference herein for the purpose of exemplifying the state of the prior art.

Although the prior art describes elastomeric materials formed by mixing mercaptoorganopolysiloxanes with alkenyl-containing polysiloxanes and organic peroxides, by mixing mercaptoorganopolysiloxanes with organic peroxides alone, or by mixing mercaptoorganopolysiloxanes with organic hydroperoxides and selected nitrogen compounds, it was not expected that useful materials, including elastomeric materials, could be provided by mixing, at room temperature, mercaptoorganopolysiloxanes and certain metal salts of carboxylic acids.

SUMMARY OF THE INVENTION

According to the present invention, novel compositions of matter are provided by mixing mercaptoorganopolysiloxanes with carboxylic acid salts of metals where the metal is selected from the group consisting of iron, copper, cobalt, manganese and nickel. Included among the compositions provided according to the invention are compositions curable to elastomers at room temperature in the presence of an oxygen-containing atmosphere such as air. Curable compositions of the invention may optionally include fillers and provide sealants which cure rapidly to elastomeric materials with non-tacky surfaces.

DESCRIPTION OF THE INVENTION

This invention relates to a curable composition consisting essentially of a material prepared by mixing:

(A) a mercaptoorganopolysiloxane consisting essentially of a combination of units selected from dimethylsiloxane units, hydroxydimethylsiloxane units, trimethylsiloxane units, units of the formula

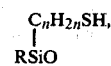

units of the formula

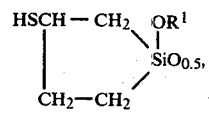

units of the formula

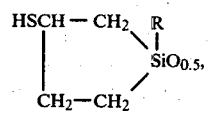

units of the formula

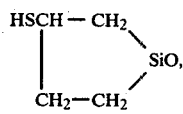

units of the formula

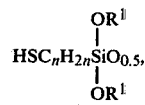

and units of the formula

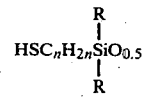

wherein: R is a monovalent radical selected from the group consisting of alkyl radicals of from 1 to 3 carbon atoms inclusive and phenyl radical; $R^1$ is a monovalent radical selected from the group consisting of alkyl radicals of from 1 to 3 carbon atoms inclusive; and n has a value of from 1 to 4 inclusive, there being in said mercaptoorganopolysiloxane an average of at least two sulfur-containing siloxane units per molecule, but not more than 10 mole percent sulfur-containing units based upon the total number of siloxane units in the mercaptoorganopolysiloxane;

(B) a filler in an amount equal to from about 0 to about 200 parts by weight per 100 parts of the weight of (A); and (C) a carboxylic acid salt of a metal where the metal is selected from the group consisting of iron, copper, cobalt, manganese and nickel in an amount equal to from about 0.01 to about 5 parts by weight per 100 parts of the weight of (A).

Incorporated by reference herein is applicants' U.S. Pat. application Ser. No. 99,298, pending filed concurrently herewith and entitled "Mercaptoorganopolysiloxane Elastomers Catalyzed by Metallic Compounds in the Presence of Peroxides".

The mercaptoorganopolysiloxanes which are useful in the practice of the present invention include those consisting essentially of dimethylsiloxane units, trimethylsiloxane units, hydroxydimethylsiloxane units, and units represented by the formulas:

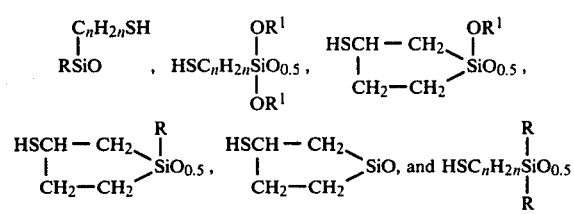

wherein: R is a monovalent radical selected from the group consisting of alkyl radicals of from 1 to 3 carbon atoms inclusive (such as methyl, ethyl or propyl) and phenyl radical; $R^1$ is selected from the group consisting of alkyl radicals having 1 to 3 carbon atoms (such as methyl, ethyl and propyl); and n has a value of from 1 to 4 inclusive, there being present in such mercaptoorganopolysiloxane an average of at least two mercapto-containing siloxane units per molecule and no more than 10 mole percent mercapto-containing units based upon the total units in the mercaptoorganopolysiloxane.

Examples of the mercaptoorganopolysiloxanes include those having "terminal" mercapto groups such as those presented by the formulas I through IV:

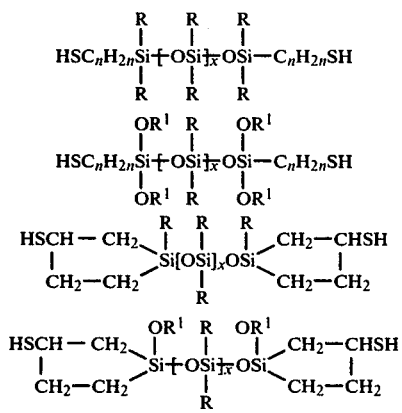

wherein R, $R^1$ and n are as defined above and x has a value of from about 18 to about 1000 and preferably about 200 to about 800, and those having pendant mercapto groups such as those represented by formulas V through VIII:

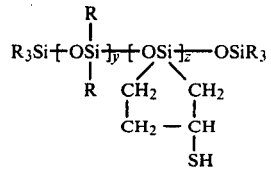

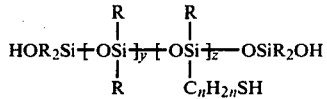

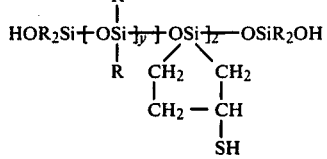

wherein n and R are as above; y+z has a value of from about 18 to about 1000 and preferably about 200 to about 800, and z is at least 2 and no more than a number providing 10 mole percent mercapto-containing siloxane units, based on total siloxane units in the mercaptoorganopolysiloxane.

The mercaptoorganopolysiloxanes of formulas I and V are known in the art as evidenced by the prior art cited herein. The mercaptosilacyclopentylpolysiloxanes of formulas III and VI and their position isomers can be prepared by the method defined in U.S. Pat. No. 3,655,713, which is hereby incorporated by reference to show the mercaptosilacyclopentylpolysiloxanes and their preparation. The mercaptoorganopolysiloxanes of formula II which contain endblocking units of the formula:

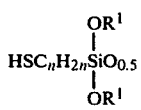

can be prepared by reacting a hydroxyl endblocked polydimethylsiloxane and a mercaptoalkyltrialkoxysilane of the formula:

in the presence of solid potassium hydroxide or potassium silanolate catalysts. The potassium silanolate catalyst is preferred for the higher viscosity polydimethylsiloxanes. The mercaptoalkyltrialkoxysilane is preferably used in excess of about 10 mole percent over stoichiometric amounts. The resulting product is essentially a polydimethylsiloxane endblocked with the units of the formula:

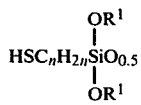

There may be some small amounts of units wherein two SiOH groups have reacted with one mercaptoalkyltrialkoxysilane molecule, but these amounts are small enough that the character of the endblocked polydimethylsiloxane is not noticeably altered.

Suitable metal salts of carboxylic acids can be represented by the formula, $$T(OR^2)_m$$

wherein: T is a metal selected from the group consisting of iron, manganese, copper, cobalt, and nickel; $R^2$ is a monovalent acyl radical; and m is either 2 or 3. Suitable monovalent acyl radicals include acetyl, propionyl, isobutyryl, stearoyl, lauroyl, 2-ethylhexanoyl (sometimes referred to as "octanoyl"), oleoyl, linoleoyl, benzoyl, napthoyl, β-benzoyl-propionyl, crotonoyl, atropoyl, palmitoyl, and cinnamoyl. The 2-ethylhexanoyl, ("octanoyl") radical is the preferred acyl radical. The most preferred catalyst is ferric octoate.

The curable compositions of the present invention can be cured by exposure to atmospheric oxygen. Preferred quantities of metal salt range from about 0.1 to about 5 parts by weight per 100 parts by weight of (A).

The compositions of this invention can be prepared by mixing at least one mercaptoorganopolysiloxane as described by one of the formulas V through VIII, wherein the average value of z is greater than 2, with a metal salt of a carboxylic acid to provide a one package product which will crosslink when exposed to air to a gel-like product or an elastomeric product depending upon the crosslink density. The one package products may have limited storage stability in a container sealed to exclude air, however, packaged compositions can be stored up to six months or more. The storage stability should be determined for each composition prepared on a small sample prior to making large amounts of composition. The suitability of the container and manner of sealing should also be determined using small samples. The length of time the composition can be stored in a sealed container can be influenced by the type of container (e.g., the material used to make the container, because some material can allow oxygen to penetrate); the tightness of the seal; and the nature of the ingredients used to make the composition. The amount of metal salt can vary from 0.01 to 5 parts by weight per 100 parts by weight mercaptoorganopolysiloxane. Fillers can be used to provide elastomeric products with improved properties.

Compositions of this invention can also be prepared by mixing at least one mercaptoorganopolysiloxane as described by one of the formulas V through VIII wherein the average value of z is greater than 2, and at least one mercaptoorganopolysiloxane as described by one of the formulas I through IV, with a metal salt to provide a one package product as described above. The amount of metal salt and the use of fillers is the same as described above. In these compositions, the amount of mercaptoorganopolysiloxane of formulas I through IV relative to the amount of mercaptoorganopolysiloxane of formulas V through VIII can vary broadly, but an average of at least 2.1 of mercapto groups per molecule of (A) should be present.

In the above compositions, the mercaptoorganopolysiloxanes which are preferred are those of formulas I through VI in which the R is methyl and n is 3.

Compositions of this invention made from mercaptoorganopolysiloxanes of formulas V and VI alone or from a combination of polymers of formulas I through IV and of polymers of formulas V and VI will result in the formation of elastomeric materials.

Fillers can be used in the compositions of this invention, but are not required. The fillers can be both treated and untreated reinforcing fillers, such as fume silica and fume silica having triorganosiloxy groups, (e.g., trimethylsiloxy groups) on the surface, carbon black or precipitated silica, and extending fillers such as crushed or ground quartz, diatomaceous earth, and calcium carbonate.

The compositions of this invention which cure to elastomers, do so rapidly at room temperature in the presence of an oxygen-containing atmosphere such as air. The resulting elastomer has a dry or non-tacky surface. The rate of cure can be accelerated with the use of heat. Air inhibition such as is observed with conventional non-mercapto-containing peroxide cured silicone rubber composition is not observed and the inhibition by various materials such as sulfur and phosphorus as observed in platinum catalyzed compositions containing aliphatic unsaturated siloxanes and SiH-containing siloxanes, is not observed. Rapidly curing elastomers of the invention are expected to be exceptionally useful sealants and can be provided in the form of mixtures of mercaptoorganopolysiloxanes (optionally including a filler) and metal salt packaged as a one package sealant system which cures upon exposure to air.

The following examples are presented for illustration purposes and should not be construed as limiting the invention.

Examples 1 through 5 demonstrate that atmospheric oxygen will cure a mixture of a mercaptoorganopolysiloxane and an iron, cobalt, copper, manganese or nickel salt of a carboxylic acid. Examples 2 through 5 also demonstrate that the mixture of metal salt and mercaptoorganopolysiloxane can be stored for moderate times in the absence of oxygen and thereafter cured by exposure to atmospheric oxygen.

EXAMPLE 1

A curable composition was prepared by mixing 0.6 parts by weight of 50 weight percent ferric octoate in mineral oil with 100 parts by weight of a mercaptoorganopolysiloxane represented by the general formula V and the average formula:

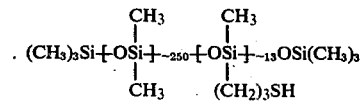

The mercaptoorganopolysiloxane had a viscosity of about 0.00106 m²/s at 27° C. and a mercapto content of 2.25 weight percent—SH (0.068 moles—SH/100 g polymer) as determined by iodine titration. The mixture was initially orange but began changing to green as the mixture set in an open cup. Upon curing, after setting for approximately 24 hours at room temperature, the sample became brown and the density of crosslinking continued to increase with time.

EXAMPLE 2

A curable composition was prepared by mixing 0.5 parts by weight of 5 weight percent cobaltous octoate in toluene with 100 parts by weight of a mercaptoorganopolysiloxane represented by the general formula V and the average formula

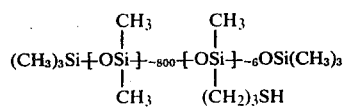

The mercaptoorganopolysiloxane had a viscosity of about 0.0389 m²/S at 23° C. and a mercapto content of 0.41 weight percent—SH (0.012 moles—SH/100 g polymer) as determined by iodine titration. The polymer was deaired, then blended with the cobaltous octoate in a sealed tube. After a sample was extruded, its surface formed a skin in 4 minutes and became tackfree in 25 minutes at room temperature exposed to air. Samples could still be extruded from the tube after 24 hours even though the consistency of the material in the tube had increased. After curing for 7 days the physical properties of the extruded sample were measured. The results obtained were as shown in the Table.

TABLE

| Durometer (Shore A) | 17 |
| Tensile Strength (MPa) | 0.72 |
| Elongation at Break | 645% |
| Modulus at 100% elongation (MPa) | 0.28 |

EXAMPLE 3

A curable composition was prepared by mixing 0.5 parts by weight of 50 weight percent cupric napthoate in mineral oil with 100 parts by weight of the mercaptoorganopolysiloxane described in Example 2 using the procedure of Example 2. An extruded sample cured to a somewhat soft and tacky elastomer after standing for three days at room temperature exposed to air. After three days, the material in the tube was partially gelled, but could still be extruded and cured.

EXAMPLE 4

A curable composition was prepared by mixing 1 part by weight of 50 percent manganous octoate in mineral oil with 100 parts by weight of the polymer described in Example 2 using the procedure described in Example 2. An extruded sample cured to a tackfree elastomer after standing for 3 days at room temperature exposed to air. After two weeks, the material in the tub had increased slightly in consistency but could still be extruded and cured.

EXAMPLE 5

A curable composition was prepared by mixing one part by weight nickelous octoate with 200 parts of a mixture of 150 parts by weight of calcium carbonate and 100 parts by weight of a mercaptoorganopolysiloxane represented by the general formula V and by the average formula

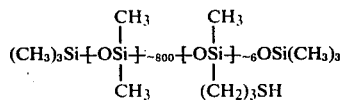

The mercaptopolysiloxane had a viscosity of about 0.0401 m²/S at 23° C. and a mercapto content of 0.41 weight percent-SH (0.012 moles—SH/100 g. polymer) as determined by iodine titration. The polymer was deaired then blended with the nickelous octoate in a sealed tube. After a sample was extruded in air a surface skin formed in 25 minutes at room temperature and became tackfree in 35 minutes. After 24 hours, the composition in the tube was uncured but after 4 days, the material could not be extruded from the tube.

The following Examples 6 through 9 are provided to illustrate the manner in which the cure rate and shelf life vary with the concentration of metal salt.

EXAMPLE 6

A curable composition was prepared by deairing 100 parts by weight of the mercaptoorganopolysiloxane described in Example 1, which was then mixed in a sealed tube with 5 parts by weight of the same polymer and 0.3 parts by weight of approximately 50 weight percent ferric octoate in mineral oil. Samples were withdrawn 10 minutes, 30 minutes, 3 days and 3 months after mixing and exposed to air. In each case, about 48 hours at room temperature were required to form a tacky skin and the samples were only partially cured after several days. The material in the tube was still flowable seven months after mixing.

EXAMPLE 7

A curable composition was prepared as in Example 6 using 0.6 parts by weight of the ferric octoate solution. Samples were withdrawn 10 minutes, 2 hours, 17 hours and 2 days after mixing and exposed to air. In each case, approximately 4 to 8 hours at room temperature were required to form a skin but the samples cured in approximately 24 to 48 hours to form a soft elastomer. The viscosity of the material in the tube remained quite low until the contents were completely consumed 17 days later.

EXAMPLE 8

The procedure of Example 6 was repeated using 1.2 parts by weight of the ferric octoate solution. Samples were withdrawn 10 minutes, 24 hours, 48 hours, 11 days and 3 months after mixing and exposed to air. In each case, the sample cured within 24 hours at room temperature except the interior of the sample withdrawn after 3 months failed to cure completely. Seven months after mixing, the composition in the tube was highly gelled.

EXAMPLE 9

The procedure of Example 6 was repeated using 2.4 parts by weight of the ferric octoate solution. Samples were withdrawn after 5 minutes, 17 hours and 3 months after mixing and exposed to air. The first sample cured with a tackfree surface after standing overnight at room temperature. The other samples were highly gelled at the time they were withdrawn.

Numerous modifications and variations in the practice of the invention are expected to occur to those skilled in the art upon consideration of the foregoing description and only such limitations as appear in the appended claims should be placed thereon.

What is claimed is:

1. A composition of matter consisting essentially of a material prepared by mixing
   (A) a mercaptoorganopolysiloxane consisting essentially of a combination of units selected from dimethylsiloxane units, hydroxydimethylsiloxane units, trimethylsiloxane units, units of the formula units of the formula

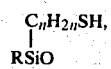

units of the formula

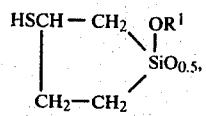

units of the formula

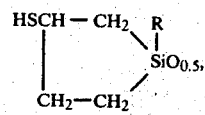

units of the formula

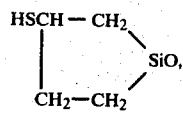

units of the formula

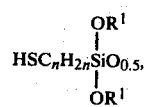

units of the formula

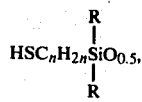

wherein: R is a monovalent radical selected from the group consisting of alkyl radicals of from 1 to 3 carbon atoms inclusive and phenyl radical: $R^1$ is a monovalent radical selected from the group consisting of alkyl radicals of from 1 to 3 carbon atoms inclusive; and n has a value of from 1 to 4 inclusive, there being in said mercaptoorganopolysiloxane an average of at least two sulfur-containing siloxane units per molecule, but not more than 10 mole percent sulfur-containing units based upon the total number of siloxane units in the mercaptoorganopolysiloxane;

(B) a filler in an amount equal to from about 0 to about 200 parts by weight per 100 parts by weight of (A); and (C) a carboxylic acid salt of a metal where the metal is selected from the group consisting of iron, cobalt, copper, manganese and nickel in an amount equal to from about 0.01 to about 5 parts by weight per 100 parts of the weight of (A).

2. The composition according to claim 1 and curable to an elastomer in which (A) consists essentially of one or more mercaptoorganopolysiloxanes selected from the group consisting of those represented by the formulas:

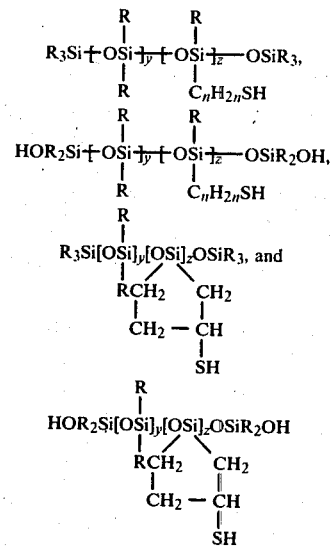

wherein $z>2$ and $y+z$ has a value of from about 18 to 1000 and wherein R and $R^1$ are as defined in claim 1.

3. The composition according to claim 2 additionally including one or more mercaptoorganopolysiloxanes selected from the group consisting of those represented by the formulas

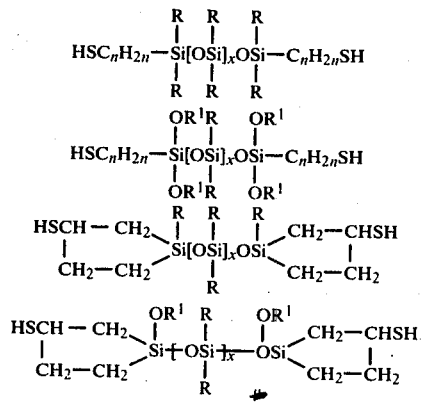

wherein x has a value of from 18 to 1000 and, in the composition, the average number of mercapto groups per molecule being at least 2.1.

4. The composition according to claim 1 in which (C) is ferric octoate.

5. The composition according to claim 1 in which (C) is cobaltous octoate.

* * * * *